United States Patent [19]

Chang

[11] 4,453,019
[45] Jun. 5, 1984

[54] USE OF MIXED METAL CATALYSTS IN THE HYDROFORMYLATION OF OLEFINS TO PRODUCE LINEAR ALDEHYDES AND ALCOHOLS

[75] Inventor: Biau-Hung Chang, Worthington, Ohio

[73] Assignee: Ashland Oil, Inc., Ashland, Ky.

[21] Appl. No.: 414,382

[22] Filed: Sep. 2, 1982

[51] Int. Cl.$^3$ .................................................. C07C 45/50
[52] U.S. Cl. ........................................ 568/454; 568/451;
502/152; 502/162; 502/166; 502/167; 502/200; 502/213
[58] Field of Search ..................... 568/451, 454, 909; 252/441

[56] References Cited

U.S. PATENT DOCUMENTS

| | | | |
|---|---|---|---|
| 3,239,566 | 5/1966 | Slaugh et al. | 568/454 |
| 3,278,612 | 10/1966 | Greeme | 568/454 |
| 4,107,079 | 8/1978 | Chevalier et al. | 568/454 |
| 4,226,845 | 10/1980 | Laine | 423/655 |
| 4,252,678 | 2/1981 | Smith | 568/454 |
| 4,306,084 | 12/1981 | Pettit | 568/451 |

OTHER PUBLICATIONS

R. M. Laine, "Applications of the Water–Gas Shift Reaction, Hydroformylation and Hydrohydroxymethylation with CO and $H_2O$", *Amer. Chem. Soc.*, pp. 6451–6454.

Hieber, W. et al., "Entstehung Mehrkerniger Carbonylferrate Aus Mehrkernigen Eisencarbonylen", *Anorg. Allg. Chem.*, 1957, 289, 324–337.

Collman et al., "Oxidative-Addition Reactions of the $NaFe(CO_4)$ Supernucleophile", *J. Amer. Chem. Soc.*, 99, 2515, 1977.

Nagel et al., "Synthesis of New Trinuclear Ions $[Ru_3(CO)_{11}]^{2-}$ And $[Os_3(CO)_{11}]^{2-}$", *J. of Organometallic Chemistry*, 219 (1981) C9–C12.

Eady et al., "Improved Syntheses of the Hexanuclear Clusters $[Ru_6(CO)_{18}]^{2-}$, and . . . $H_2Ru_6(CO)_{18}$", 1980, *J.C.S. Dalton*, 383–392.

Inkrott et al., "Stepwise Deprotonation of $H_4Ru_4(CO)_{12}$: High-Yield Synthesis and Carbon-13 NMR Spectra of $H_3Ru_4(CO)_{12}^{31}$ and $H_2Ru_4(CO)_{12}^{-}$, *Inorg. Chem.*, vol. 18, No. 10, 1979, 2817–2821.

Inkrott et al., "The New Cluster Dianion $H_2Ru_4(CO)_{12}{}^{2-}$, Simple High-Yield, Stepwise Deprotonation of $H_4Ru_4(CO)_{12}$", *J. Amer. Chem. Soc.*, 100:12, Jun. 7, 1978, 3954–3955.

P. F. Jackson et al., "$H_2Ru_6(CO)_{18}$,$[HRu_6(CO)_{18}{}^-$, and $[Ru_6(CO)_{18}]^{2-}$: a Simple High Yield Route to . . . $[Ph_3MeP]_2]Ru_6(CO)_{18}]$", J.C.S. Chem. Comm., 1979, 735–736.

Nagel et al., "High Yield Syntheses of New Tetraruthenium . . . of $H_2Ru_4(CO)_{13}$", *J.C.S. Chem. Comm.*, 1980, 530–531.

*Primary Examiner*—Warren B. Lone
*Attorney, Agent, or Firm*—Wood, Herron & Evans

[57] ABSTRACT

A process for producing linear aldehydes or alcohols from olefins using a mixed transition metal hydroformylation catalyst wherein the catalyst comprises a mixture of transition metal compounds wherein the first component is an anionic transition metal catalyst having a charge of at least −2. The formula of the anionic compound is generally defined as $M^{+n}[H_yA_xL_z]^{-n}$ Wherein A represents Fe, Ru, Os, W, Cr, Co, Rh, Ir or Mo, M is a cationic species, n is an integer greater than or equal to 2, x is an integer greater than or equal to 1, y is an integer greater than or equal to 0 and z is an integer generally corresponding to the number of available coordination bonding sites of A. The second component is a Group VIII compound, preferably a halide or carbonyl of the Group VIII compound. These compounds exhibit high selectivity toward linear products.

14 Claims, No Drawings

USE OF MIXED METAL CATALYSTS IN THE HYDROFORMYLATION OF OLEFINS TO PRODUCE LINEAR ALDEHYDES AND ALCOHOLS

BACKGROUND OF THE INVENTION

The present invention relates to a process for the hydroformylation of olefins to produce aldehydes and alcohols. The present invention more particularly relates to such a process in which anionic transition metal complex catalysts are used which are extremely selective toward straight chain products. The present invention more particularly relates to the use of mixed metal complexes as hydroformylation catalysts.

Aldehydes and alcohols are extremely useful as general purpose solvents, as surfactants and as precursors to many other useful chemicals. Due to the extent to which these compounds are used, it is important that such compounds be biodegradable. One important factor effecting the biodegradability of aldehydes and alcohols is the linearity of the molecule. Linear aldehydes and alcohols are more easily biodegraded than branch-chain aldehydes and alcohols. In addition, certain straight chain aldehydes and alcohols are extremely useful in particular applications.

One particular straight chain aldehyde which has particular utility is n-butyraldehyde. This aldehyde can be dehydrated to form 2-ethyl hexanol which is useful as a gasoline additive or the aldehyde can be esterified with phthalic anhydride to produce dioctylphthalate which is used for plasticizing polyvinyl chloride resins.

The straight chain alcohols or esters of the straight chain alcohols are useful as surfactants or soaps which are biodegradable. Particularly useful are $C_{12}$ to $C_{18}$ alcohols and the esters of these alcohols.

One method of producing aldehydes and alcohols is the hydroformylation of olefins. Hydroformylation is an old reaction and is used commercially to prepare both straight and branch-chain aldehydes and alcohols. In this reaction, an olefin is reduced by the addition of carbon monoxide and hydrogen to form an aldehyde. This reaction can be carried further until the aldehyde is reduced to an alcohol. This is further explained in U.S. Pat. No. 3,876,672 which is incorporated herein by reference.

The hydroformylation reaction generally requires a catalyst. In the past, typical catalysts have included cobalt carbonyl, rhodium carbonyl, nickel, and platinum complexes, as well as monovalent ruthenium cluster complexes. A problem encountered with most of these prior art catalysts was the poor selectivity toward linear aldehydes or alcohols.

Therefore, it is an object of the present invention to disclose a process for the hydroformylation of olefins to produce a high percentage of linear aldehydes or alcohols and low percentage of branch-chain aldehydes or alcohols.

SUMMARY OF THE INVENTION

The present invention comprises a method of forming aldehydes according to the following reaction:

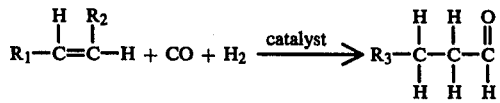

wherein the catalyst is a mixed transition metal catalyst comprised of a first transition metal compound selected from the group consisting of Group VIII transition metals and preferably, Group VIII transition metal halides or carbonyls and a second transition metal compound having the following general formula:

$$M^{+n}[H_y A_x L_z]^{-n}$$

wherein:

A represents Fe, Ru, Os, W, Cr, Co, Rh, Ir and Mo and preferably Fe, Ru, Os, W and Mo;

M represents a cationic moiety; n represents an integer greater than or equal to 2;

n represents an integer greater than or equal to 2;

y represents an integer greater than or equal to 0;

x represents an integer greater than or equal to 1;

L represents a ligand and preferably, carbonyl or halide; and z represents an integer less than or equal to the number of available coordination bonding sites of the transition metal complex. This reaction can be carried further whereby the aldehyde is reduced to form an alcohol.

DETAILED DESCRIPTION OF THE INVENTION

The hydroformylation reaction is an addition reaction in which carbon monoxide and hydrogen are reacted with an olefin to produce a saturated aldehyde. In other words, carbon monoxide and hydrogen are added to the olefin and the olefin reduced. The olefin can be reacted with carbon monoxide in the presence of hydrogen and a catalyst, or the olefin can be reacted with an excess of carbon monoxide and water in the presence of a catalyst. When carbon monoxide and water are used in the reaction, the water is simply a source of hydrogen, reacting with the carbon monoxide to form hydrogen and carbon dioxide. Hydrogen is thereby provided to react together with additional carbon monoxide upon the olefin. In either case, there is a hydrogen source available to react in combination with carbon monoxide upon the olefin. This reaction can be continued and available hydrogen would react with the aldehyde to produce an alcohol. The formation of the alcohol is encouraged by altering reaction conditions such as reaction time, pressure and temperature.

The hydroformylation reaction is shown by the following reaction formula (I):

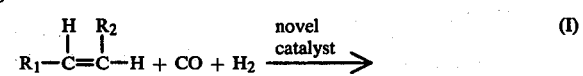

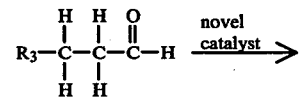

-continued $$R_3-\underset{\underset{H}{|}}{\overset{\overset{H}{|}}{C}}-\underset{\underset{H}{|}}{\overset{\overset{H}{|}}{C}}-\underset{\underset{H}{|}}{\overset{\overset{H}{|}}{C}}-OH$$

wherein $R_1$ represents alkyl, substituted alkyl, aryl, or substituted aryl and $R_2$ represents hydrogen, alkyl, substituted alkyl, aryl or substituted aryl. As shown in formula (I), this reaction can be carried further causing the addition of hydrogen to the formed aldehyde forming a linear alcohol.

Even if when $R_2$ is not hydrogen, the novel catalyst of the present invention will cause the double bond in the olefin reactant to migrate to form a linear aldehyde. $R_1$ or $R_2$ must, however, be either hydrogen or an unsubstituted alkyl group or the reaction will proceed at a very slow rate. $R_3$ will represent alkyl, substituted alkyl, aryl or substituted aryl and its formula will be determined by the make-up of $R_1$ and $R_2$. Thus, for example, if $R_1$ and $R_2$ are methyl groups, the hydroformylation will produce an aldehyde in which $R_3$ is an ethyl group. The double bond in the olefin will have migrated one carbon atom to form n-pentaldehyde.

The hydroformylation reaction is applicable to a wide variety of unsaturated compounds, including compounds containing more than one ethylenic group. Since difficulty has been experienced where the olefin is highly branched, two substituents of the olefinic group should be hydrogen as is shown in formula I. Hydroxyl or halogen substituents must be removed from the double bond by at least two carbon atoms and preferably not be present at all since they inactivate the catalyst in some situations.

Substituents which do not substantially interfere with the hydroformylation reaction include alkyl, aryl carbonyl, aryl, $C_1$-$C_9$ alkoxycarbonyl, aralkyl, $C_1$-$C_9$ alkaryl, $C_1$-$C_9$ alkoxy and aryloxy. Aryl groups present may also be substituted by any of the other non-interfering substituents. The unsaturated compounds may contain up to 20 carbon atoms.

In order to obtain the full benefit of the present invention, $R_1$ and $R_2$ should be a straight chain $C_1$-$C_9$ alkyl group or $R_1$ or $R_2$ should be hydrogen. If $R_1$ and $R_2$ would be hydrogen, the product must necessarily be straight chain, i.e., propanal. Therefore, if ethylene is the olefin reactant, the benefit of using the catalysts of the present invention is not appreciated. When ethylene is reacted, a more reactive catalyst which is not selected toward the linear product should be used.

The preferred olefin of the present invention should have the following general formula:

$$R_4-\underset{\underset{H}{|}}{\overset{\overset{H}{|}}{C}}=\underset{\underset{H}{|}}{\overset{\overset{}{|}}{C}}-H \qquad (II)$$

wherein $R_4$ is a straight chain $C_1$-$C_{18}$ alkyl. This olefin should react quickly with high selectivity toward linear product.

In the event a di-olefin were reacted to form a dialdehyde or dialcohol, the olefin should have the following general Formula III.

$$\underset{\underset{}{}}{CH_2}=\underset{\underset{}{|}}{\overset{\overset{H}{|}}{C}}-R_5-\underset{\underset{}{|}}{\overset{\overset{H}{|}}{C}}=CH_2 \qquad (III)$$

wherein $R_5$ is an alkyl, substituted alkyl, aryl or substituted aryl, and preferably, a straight chain $C_1$-$C_9$ or higher alkyl.

Preferred olefins include: propylene, butene-1, pentene-1, hexene-1, heptene-1, octene-1, nonene-1, decene-1, undecene-1, dodecene-1, tridecene-1, tetradecene-1, pentadecene-1, hexadecene-1, heptadecene-1, octadecene-1, nonadecene-1, eicosene, 1,5-hexadiene, 1,6-heptadiene, 1,7-octadiene, 1,8-nonadiene, 1,9-decadiene, 1,10-undecadiene, and 1,11-dodecadiene.

Novel Hydroformylation Catalysts

Novel hydroformylation catalysts of the present invention are mixtures of transition metals wherein two transition metal compounds are combined in the reaction vessel. The first transition metal compound is a neutral or anionic transition metal compound wherein the metal is selected from Group VIII of the Periodic Table. Preferably, these should be halides or carbonyls of the transition metals. Included are mono-, di- and multinuclear transition metal compounds as well as organotransition metal compounds.

Examples of these compounds would include $RhCl_3$, $RuCl_3$, $(Rh)(CO)_2Cl_2$, $Co_2(CO)_8$, $Rh_6(CO)_{16}$, $Ru_3(CO)_{12}$, $Ir_4(CO)_{12}$, $Os_3(CO)_{12}$, $Fe_3(CO)_{12}$, $Co_2Rh_2(CO)_{12}$, $HRh(CO)(PPh_3)_3$, $H_2Ru_4(CO)_{13}$, $H_2Ru_6(CO)_{18}$, $H_2PtCl_6$, $H_4Ru_4(CO)_{12}$, $PdCl_2(PPh_3)_2$, $HCoRu_3(CO)_{13}$, and so on. Preferably, the transition metal compound will be a halide or a carbonyl.

The second transition metal component of the catalyst of the present invention has the following general formula:

$$M^{+n}[H_yA_xL_z]^{-n} \qquad (IV)$$

wherein

A represents Fe, Ru, Os, W, Mo, Cr, Co, Rh and Ir;
M is a cationic species;
n is an integer greater than or equal to 2;
x is an integer greater than or equal to 1;
y is an integer greater than or equal to 0; and
z is an integer less than or equal to the available coordination bonding sites of the transition metal complex represented by $A_x$.

Typically n will not exceed 6, y will not exceed 4 and is usually 2 or less, x will not exceed about 36. In theory these upper limits may be exceeded, but known species generally fall within these limits. The ligands represented by L include any ligand which will bond with the transition metal complexes and which will not interfere with the hydroformylation reaction. Ligands specifically suitable for use in the present invention include: trialkyl phosphines, trialkyl arsines, trialkyl antimonies, trialkyl bismuths, triaryl phosphines, triaryl arsines, triaryl antimonies, triaryl bismuths, tertiary amines, carbon monoxide and halides.

M can represent any cationic species which will bond to the transition metal anionic complex and will not interfere with the hydroformylation reaction. Generally, M will represent one or more metals preferably selected from Group IA and Group IIA or an organic cation such as iminium, ammonium, phosphonium or arsenium.

The second anion transition metal component of this catalyst can be prepared by the reduction of a neutral species such as metal carbonyls or the deprotonization of hydride metal compounds.

For example, $[(Ph_3P)_2N]_2[Fe_3(CO)_{11}]$ can be prepared from $Fe_3(CO)_{12}$. More specifically, the $Fe_3(CO)_{12}$ can be reacted with KOH dissolved in absolute methanol at room temperature for about 28 hours. The addition of $(Ph_3P)_2NCl$ causes $[(Ph_3P)_2N]_2[Fe_3(CO)_{11}]$ to precipitate out of solution. This is further described in Hieber, W.; Brendel, G. Z., *Anorg. Allg. Chem.*, 1957, 289, 324–337.

As discussed in Collman et al, *Oxidative-Addition Reactions of the $Na_2Fe(CO)_4$ Supernucleophilic*, J. American Chem. Soc., 94, 2515 (1977), $Na_2Fe(CO)_4$ and analogous compounds can be prepared by the reduction of $Fe(CO)_5$ using sodium dispersed in benzophenone. $K_2Fe(CO)_4$ can be prepared in a similar manner.

The preparation of $[Os_3(CO)_{11}]^{2-}$ is discussed in Nagel et al, *Synthesis of New Trinuclear Ions $[Ru_3(CO)_{11}]^{2-}$, and $[Os_3(CO)_{11}]^{2-}$* in *J. of Organometallic Chemistry*, 219 (1981) C9–C12. These compounds are prepared by the reduction of the neutral species using, for example, an alkali metal benzophenone solution.

The anionic ruthenium compounds may be produced according to numerous methods disclosed in the following articles: Eady et al, *Improved Synthesis of the Hexanuclear Clusters $[Ru_6(CO)_{18}]^{2-}$, $HRu_6(CO)_{18}]^-$, and $H_2Ru_6(CO)_{18}$*, 1980 *J.C.S. Dalton*, 383; Inkrott et al, *Stepwise Deprotonation of $H_4Ru_4(CO)_{12}$: High-Yield Synthesis and Carbon-13 NMR Spectra of $H_3Ru_4(CO)_{12}^-$ and $H_2Ru_4(CO)_{12}^{2-}$*, 18 *Inorganic Chemistry* 2817 (1979); Inkrott et al, *The New Cluster Dianion $H_2Ru_4(CO)_{12}^{2-}$*, 100:12 *Journal of the American Chemical Society* 3954 (1978); P. F. Jackson et al, *$H_2Ru_6(CO)_{18}$, $[HRu_6(CO)_{18}]^-$ and $[Ru_6(CO)_{18}]^{2-}$: A Simple High Yield Route to These Clusters and the X-Ray Structure of $[Ph_3MeP]_2[Ru_6(CO)_{18}]$*, *J.C.S. Chem. Com.*, 735 (1979); Nagel et al, *High Yield Synthesis of New Tetraruthenium Carbonylates: $[Ru_4(CO_{13})]^{2-}$, $[HRu_4(CO)_{13}]^-$, and $[Ru_4(CO)_{12}]^{4-}$*, *J.C.S. Chem. Com.*, 530 (1980); which are incorporated herein by reference to indicate the state of the art in ruthenium complex chemistry.

Anionic ruthenium compounds are formed, for example, by the stepwise deprotonation of $H_4Ru_4(L)_z$ according to the following formula:

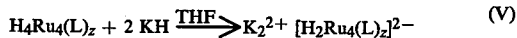

$$H_4Ru_4(L)_z + 2\,KH \xrightarrow{THF} K_2^{2+}\,[H_2Ru_4(L)_z]^{2-} \quad (V)$$

wherein L represents a ligand and z is an integer corresponding to the number of available coordination bonding sites. When $H_2Ru_4(CO)_{12}^{2-}$ is being formed, the reaction is conducted by mixing the KH with the $H_4Ru_4(CO)_{12}$ in THF for about one half an hour at 55° C. and an additional 24 hours at ambient temperatures, both in an inert atmosphere. Removal of the solvent in vacuo yields $K_2[H_2Ru_4(CO)]_{12}$. The reaction product can be further reacted with two equivalents of $[(Ph_3P_2)N]Cl$ or $[(n-C_4H_9)_4N]Br$ to produce $[(Ph_3P)_2N]_2[H_2Ru_4(CO)_{12}]$ and $[(n-C_4H_9)_4N]_2[H_2Ru_4(CO)_{12}]$, respectively.

Another method of producing the catalysts of the present invention is the controlled reduction of $Ru_3(L)_z$ using potassium-benzophenone according to the following reaction:

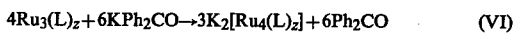

$$4Ru_3(L)_z + 6KPh_2CO \rightarrow 3K_2[Ru_4(L)_z] + 6Ph_2CO \quad (VI)$$

The reaction should be conducted in a dry, inert atmosphere, such as argon or nitrogen. A more specific example is the reduction of dodecarbonyltriruthenium by treatment with 1.6 equivalents of potassium-benzophenone (10% excess) in THF. A deep red solution is produced after stirring the solution overnight at −78° C. and for 24 hours at 25° C. $K_2[Ru_4(CO)_{13}]$ is then obtained from this solution by precipitation with $CH_2Cl_2$. The deep red reaction mixture can be further reacted with $[(Ph_3P)_2N]Cl$ and precipitated with $CH_2Cl_2$ to yield $[(Ph_3P)_2N]_2[Ru_4(CO)_{13}]$.

Dianionic tungsten, molybdenum, chromium, cobalt, rhodium and iridium compounds can also be formed using similar methods. Specifically, neutral compounds can be reduced using appropriate reducing agents such as sodium amalgam in tetrahydrofuran.

The ratio based on moles of transition metals of the first component and the second component, the dianionic component, will vary generally from about 1:1 to about 1:10. When the second or dianionic component is less than 50 percent of the total mixture, the selectivity of the catalyst decreases. Preferably, the ratio should be at about 1:5. These ratios are all based on moles of transition metal atoms.

The mixed metal catalyst is formed by simply mixing the two components in the reaction vessel. During the hydroformylation reaction, it is believed that a reaction takes place in which a mixed metal cluster is formed. No special reaction conditions are required in order to produce a catalyst which is highly selective.

The catalysts can be preformed by simply mixing the first and second component in the desired ratio and in a compatible solvent, such as anhydrous 1,2-dimethoxyethane, and allowing the mixture to set at room temperature overnight or at a higher temperature. The mixed transition metal catalyst will form during this period. The catalyst can be added in solution without separating the catalyst from any by-products which may be formed.

Hydroformylation Reaction

The hydroformylation reaction is conducted by mixing the olefin, carbon monoxide, and a hydrogen source, i.e., hydrogen or water together with the two components of the catalyst, and optionally, a solvent in a continuous or batch-type reactor. Preferably, the solution is heated and maintained under increased pressure.

While the reaction will occur at room temperature, it is preferred to heat and maintain the reaction mixture at 120°–200° C. In general, if the temperature is decreased, the rate of the reaction decreases. But, as the temperature is increased above 200° C., the selectivity toward linear aldehydes and alcohols decreases. In addition, the increase in temperature increases the difficulty of controlling the reaction to obtain primarily aldehydes as opposed to alcohols should this be desired.

Preferably, for the production of straight chain aldehydes, the pressure of the reaction should be maintained at between 500 psi to 2500 psi. This combined with a mixing force causes the carbon monoxide to go into solution. The higher pressure also tends to increase both the reaction rate and the selectivity of the reaction toward linear products. However, increased pressure also promotes the continuation of the reaction to produce alcohols.

The reaction time will vary depending on the temperature and pressure. Generally, the reaction time is maintained between 0.5–10 hours. An increase in time will cause an increase in the production of alcohol. It should be noted that in order to obtain only linear aldehydes, the reaction time is kept to a minimum which in turn does not provide time for most of the olefin to react. This can be more fully appreciated by considering the examples provided below.

To increase the production of alcohol as opposed to the aldehyde, the reaction temperature should be above 160° C.; the pressure should be above 800 psi and the reaction time from 3–5 hours or longer. Analysis of the reaction products will enable one of ordinary skill in the art to select the preferred reaction conditions for a particular olefin and catalyst.

The reaction may be run with or without a solvent. Suitable solvents include aldehydes, alcohols, ethers, esters, ketones, nitriles, aromatic hydrocarbons, aliphatic hydrocarbons, and chlorocarbons. Particularly suitable solvents include tetrahydrofuran, dibutyl ether, diethyl ether, dioxane, 2-methoxyethyl ether, 1,2-dimethoxyethane, butyl alcohol, ethyl alcohol, ethylene glycol, isobutyl alcohol, n-butyraldehyde, ethyl acetate, amyl acetate, ethyl butyrate, methyl benzoate, acetone, methyl ethyl ketone, methyl isobutyl ketone, acetonitrile, propionitrile, benzonitrile, chloroform, ethylene dichloride, methylene chloride, chlorobenzene, the chlorotoluenes, benzene, toluene, xylene, hexane, heptane, octane, cyclohexane, and methylcyclohexane.

The reaction can be conducted in a continuous or batch-type reactor. Only the batch-type reaction is described below. However, this will enable one of ordinary skill in the art to perform the hydroformylation reaction in a continuous reactor.

The reaction vessel containing the olefin and the two components of the catalyst system is thoroughly flushed with carbon monoxide and then pressurized with carbon monoxide and hydrogen. If the olefin is a gas at room temperature, it is added with the carbon monoxide and hydrogen. A sufficient quantity of each gas is added to give the desired molar ratio and the desired pressure at the chosen reaction temperature. An excess of carbon monoxide and hydrogen are generally added. Since the reaction pressure is altered by increasing or decreasing the quantity of reaction gases introduced into the reaction vessel, the preferred amount of gas is a function of the reaction pressure. The system is then heated with agitation until the reaction is complete. As the reaction proceeds, more hydrogen or carbon monoxide can be added periodically to maintain the pressure in the desired range.

If the hydrogen source is water, the above description is modified by adding water with the catalyst and hydrogen gas is not introduced. The water will react with the carbon monoxide in the presence of the catalyst to produce the needed hydrogen. This is referred to as a water-gas shift reaction.

These reactions can be further appreciated by reference to the examples provided below. These examples provide evidence of utility as well as a further description of the invention. Attention should be focused on the selectivity toward the linear product obtained of these novel catalysts. As can be seen by looking at these examples, the selectivity and the yield toward a linear product are substantially improved when a catalyst of the present invention is used.

EXAMPLE 1

In a 300 ml. hastelloy C autoclave reactor, 0.214 g (0.34 mmol) of ruthenium carbonyl ($Ru_3(CO)_{12}$), 0.81 g (2.34 mmol) of disodium tetracarbonylferrate.dioxane ($Na_2Fe(CO)_4.1.5(C_4H_8O_2)$), 2 ml. (18.3 mmol) of 1-pentene and 80 ml. of anhydrous tetrahydrofuran (THF) are placed. The reactor is sealed, flushed three times with carbon monoxide, pressurized with 1600 psig of an approximately equimolar mixture of carbon monoxide and hydrogen and heated to 180° C. with stirring. The reaction is allowed to proceed for one hour. The reactor is cooled and the reaction products are drawn out and analyzed with GLC. It is found that 15% of pentene is converted to n-hexanal with selectivity of 92%.

EXAMPLE 2

In a 300 ml. hastelloy C autoclave reactor, 0.1576 g (0.212 mmol) of $H_4Ru_4(CO)_{12}$, 0.4801 g. (1.387 mmol) of $Na_2Fe(CO)_4.1.5(C_4H_8O_2)$, 2 ml. (18.3 mmol) of 1-pentene and 80 ml. of anhydrous THF are placed. The reactor is sealed, flushed three times with carbon monoxide, pressurized with 1750 psig of an approximately equimolar mixture of carbon monoxide and hydrogen, and heated to 160° C. with stirring. The reaction is allowed to proceed for three hours. The reactor is cooled and the reaction products are drawn out and analyzed with GLC. It is found that 68% of pentene is converted to a mixture of n-hexanal and n-hexanol with selectivity of 91%.

EXAMPLE 3

In a 300 ml. hastelloy C autoclave reactor, a 1,2-dimethoxyethane solution of $Ru_3(CO)_{12}/Na_2W_2(CO)_{10}$ which is formed by mixing $Ru_3(CO)_{12}$ (0.1476 g., 0.231 mmol) with $Na_2W_2(CO)_{10}$ (2.31 mmol) in 20 ml. anhydrous 1,2-dimethoxyethane at room temperature for 24 hours, 2 ml. (18.3 mmol) of 1-pentene and 60 ml. of anhydrous 1,2-dimethoxyethane are placed. The reactor is sealed, flushed three times with carbon monoxide, pressurized with 1300 psig of an approximately equimolar mixture of carbon monoxide and hydrogen, and heated to 180° C. with stirring. The reaction is allowed to proceed for one hour. The reactor is cooled and the reaction products are drawn out and analyzed with GLC. It is found that 53% of pentene is converted to a mixture of n-hexanal and n-hexanol with selectivity toward linear products of 91%.

EXAMPLE 4

In a 300 ml. hastelloy C autoclave reactor, 0.8005 g. (2.341 mmol) of dicobalt octacarbonyl ($Co_2(CO)_8$), 0.8462 g. (2.445 mmol) of $Na_2Fe(CO)_4.1.5(C_4H_8O_2)$, 2 ml. (18.3 mmol) of 1-pentene, and 80 ml. of anhydrous THF are placed. The reactor is sealed, flushed three times with carbon monoxide, pressurized with 1500 psig of an approximately equimolar mixture of carbon monoxide and hydrogen and heated to 160° C. with stirring. The reaction is allowed to proceed for one hour. The reactor is cooled and the reaction products are drawn out and analyzed with GLC. It is found that 10% of pentene is converted to n-hexanal with selectivity of 80.1%.

EXAMPLE 5

In a 300 ml. hastelloy C autoclave reactor, 0.154 g. (0.085 mmol) of $[(Ph_3P)_2N]_2H_2Ru_4(CO)_{12}$, 0.0268 g. (0.0785 mmol) of $Co_2(CO)_8$, 3 ml. (19.1 mmol) of 1-octene and 80 ml. of anhydrous 1,2-dimethoxyethane are placed. The reactor is sealed, flushed three times with carbon monoxide, pressurized with 820 psig of an approximately equimolar mixture of carbon monoxide and hydrogen, and heated to 180° C. with stirring. The reaction is allowed to proceed for one hour. The reactor is cooled and the reaction products are drawn out and analyzed with GLC. It is found that 31.1% of octene is converted to n-nonanal with selectivity of 97.1%.

As can be seen from the preceding examples, use of the mixed metal catalysts of the present invention produces aldehydes and alcohols with a high selectivity towards the linear products. This is extremely critical when a catalyst is used having a relatively low conversion rate. Once the olefin is passed through the reactor, if it is reacted to produce an unwanted product, it cannot be passed a second time through the reactor and reacted expecting to get the desired product. Once the side reaction occurs, the unwanted product must be discarded. Therefore, when conversions are not near 100%, it is critical that the selectivity be extremely high, 80–90% in order to make the process commercially feasible. Otherwise, excessive amounts of unwanted byproducts are created and have to be discarded, making the process extremely expensive.

The preceding examples should be compared with Example 6 where a catalyst is formed from a neutral ruthenium compound and a monoanionic cobalt compound. Using this catalyst, the selectivity was substantially poorer than the results obtained by the catalysts used in Examples 1–5.

EXAMPLE 6

In a 300 ml. hastelloy C autoclave reactor, 0.184 mmol [(Ph$_3$P)$_2$N]CoRu$_3$(CO)$_{13}$ prepared from Ru$_3$(CO)$_{12}$ and [(Ph$_3$P)$_2$N]Co(CO)$_4$, 19.1 mmol 1-octene, were placed. The reactor is sealed, flushed three times with carbon monoxide, pressurized with 1000 psig of an approximately equimolar mixture of carbon monoxide and hydrogen and heated to 100° C. with stirring. The table below gives the results taken at various time intervals.

| React. Time | Conver. % | Linear Ald. | Linear Alcohol | Branched Ald. | Branched Alcohol |
|---|---|---|---|---|---|
| 1 hr. | 8.2% | 63.4% | 0% | 36.6% | 0% |
| 3 hr. | 16.6% | 58.2% | 0% | 41.8% | 0% |
| 5 hr. | 25.6% | 56.0% | 1.0% | 43.0% | 0% |

A comparison of Example 6 with the preceding examples demonstrates the superiority of the particular mixed metal catalyst of the present invention.

Having thus described my invention, I claim:

1. The method of forming a linear aldehyde from C$_3$–C$_{25}$ olefin comprising reacting said olefin with CO and a hydrogen source in the presence of a catalyst, said catalyst comprising a hydroformylation catalyst composition comprising in admixture a first transition metal compound and a second transition metal compound wherein said first transition metal compound is selected from the group consisting essentially of anionic and neutral Group VIII transition metal compounds; and
wherein said second transition metal compound has the following general formula:

$$M^{+n}[H_yA_xL_z]^{-n}$$

wherein
n is an integer greater than or equal to 2;
M is a cationic species;
A is a transition metal selected from the group consisting essentially of Ru, Os, Fe, Cr, Co, Rh, Ir, Mo and W;
x is an integer greater than or equal to 1;
L is a ligand;
z is an integer less than or equal to the available coordination bonding sites of A; and
y is an integer greater than or equal to 0.

2. The method of forming a linear alcohol from C$_3$–C$_{25}$ olefins comprising reacting said olefin with CO and a hydrogen source in the presence of a catalyst, said catalyst comprising a hydroformylation catalyst composition comprising in admixture a first transition metal compound and a second transition metal compound wherein said first transition metal compound is selected from the group consisting essentially of anionic and neutral Group VIII transition metal compounds; and
wherein said second transition metal compound has the following general formula:

$$M^{+n}[H_yA_xL_z]^{-n}$$

wherein
n is an integer greater than or equal to 2;
M is a cationic species;
A is a transition metal selected from the group consisting essentially of Ru, Os, Fe, Cr, Co, Rh, Ir, Mo and W;
x is an integer greater than or equal to 1;
L is a ligand;
z is an integer less than or equal to the available coordination bonding sites of A; and
y is an integer greater than or equal to 0.

3. The method claimed in claim 1 wherein said first transition metal compound is carbonyl.

4. The method claimed in claim 1 wherein said first transition metal is a metal halide.

5. The method claimed in claim 1 wherein said first transition metal compound includes a transition metal selected from the group consisting of Rh, Os and Ru.

6. The method claimed in claim 1 wherein the molar ratio of the transition metals of said first transition metal compound to said second transition metal compound is from about 1:10 to 1:1.

7. The method claimed in claim 6 wherein said ratio is from about 1:1 to about 1:5.

8. The method claimed in claim 1 wherein said olefin, carbon monoxide and hydrogen source are reacted at from about 100° to about 200° C. at a pressure of from about 500 psi to about 2500 psi and from between 0.5 to about 10 hours.

9. The method claimed in claim 1 wherein L represents a ligand selected from the group consisting of trialkyl phosphenes, trialkyl arsenes, trialkyl antimonies, trialkyl bismuths, triaryl phosphenes, triaryl arsenes, triaryl antimonies, triaryl bismuths, carbon monoxide and tertiary amines.

10. The method claimed in claim 1 wherein m represents a cationic species selected from the group consisting of Group Ia and Group IIa metals and ammonium, phosphonium and arsenium.

11. The method claimed in claim 2 wherein said olefin, carbon monoxide and hydrogen source are reacted at from about 100° to about 200° C. at a pressure of from about 500 psi to about 2500 psi and from between 0.5 to about 10 hours.

12. The method claimed in claim 2 wherein L represents a ligand selected from the group consisting of trialkyl phosphenes, trialkyl arsenes, trialkyl antimonies, trialkyl bismuths, triaryl phosphenes, triaryl arsenes, triaryl antimonies, triaryl bismuths, carbon monoxide and tertiary amines.

13. The method claimed in claim 2 wherein m represents a cationic species selected from the group consisting of Group Ia and Group IIa metals and ammonium, phosphonium and arsenium.

14. The method of forming a linear aldehyde from $C_3$–$C_{25}$ olefin comprising reacting said olefin with CO and a hydrogen source in the presence of catalyst, said catalyst comprising a hydroformylation catalyst composition comprising in admixture:

a first transition metal compound wherein said transition metal is selected from the group consisting essentially of Fe, Ru, Os, Co, Rh, Ir, Ni, Pd and Pt, and wherein said first transition metal compound is a halide or a carbonyl compound;

a second transition metal compound having the following general formula:

$$M^{+n}[H_yA_xL_z]^{-n}$$

wherein
n is an integer greater than or equal to 2;
M is a cationic species;
A is a transition metal selected from the group consisting essentially of Ru, Os, Fe, Mo, and W;
x is an integer greater than or equal to 1;
L is a ligand;
z is an integer less than or equal to the available coordination bonding sites of A; and
wherein the molar ratio of the transition metals of said first transition metal compound to said second transition metal compound is from about 1:1 to about 1:10 thereby providing an effective hydroformylation catalyst.

* * * * *